US009427193B2

(12) United States Patent
Chiang (10) Patent No.: US 9,427,193 B2
(45) Date of Patent: *Aug. 30, 2016

(54) DIGITAL INTEGRATION WITH DETECTOR CORRECTION

(75) Inventor: Alice Chiang, Weston, MA (US)

(73) Assignee: Teratech Corporation, Burlington, MA (US)

( * ) Notice: Subject to any disclaimer, the term of this patent is extended or adjusted under 35 U.S.C. 154(b) by 364 days.

This patent is subject to a terminal disclaimer.

(21) Appl. No.: 13/604,260

(22) Filed: Sep. 5, 2012

(65) Prior Publication Data

US 2012/0328073 A1     Dec. 27, 2012

Related U.S. Application Data

(62) Division of application No. 12/628,774, filed on Dec. 1, 2009, now Pat. No. 8,270,564.

(60) Provisional application No. 61/118,793, filed on Dec. 1, 2008.

(51) Int. Cl.
*A61B 6/00* (2006.01)
*A61B 6/03* (2006.01)
*A61B 6/02* (2006.01)

(52) U.S. Cl.
CPC ............. *A61B 6/032* (2013.01); *A61B 6/4233* (2013.01); *A61B 6/5264* (2013.01); *A61B 6/027* (2013.01)

(58) Field of Classification Search
CPC .. A61B 6/032; A61B 6/5264; A61B 6/4233; A61B 6/027; G01N 23/046; G01T 1/2928

USPC ............... 378/4–20, 98.8, 116; 250/370.08, 250/370.09, 370.11

See application file for complete search history.

(56) References Cited

U.S. PATENT DOCUMENTS

| 5,265,013 | A | 11/1993 | King et al. |
|---|---|---|---|
| 5,844,961 | A | 12/1998 | McEvoy et al. |
| 6,272,201 | B1 | 8/2001 | Pan |
| 6,445,763 | B1 | 9/2002 | Hoffman |
| 6,586,743 | B1 | 7/2003 | Overdick et al. |
| 6,859,514 | B2 | 2/2005 | Hoffman |
| 6,901,135 | B2 | 5/2005 | Fox et al. |
| 6,949,746 | B2 | 9/2005 | Stierstorfer |
| 7,539,284 | B2 | 5/2009 | Besson |
| 7,579,584 | B2 | 8/2009 | Ritter et al. |
| 8,270,564 | B2 * | 9/2012 | Chiang ..................... 378/19 |
| 2008/0069298 | A1 | 3/2008 | Hoffman et al. |
| 2008/0118023 | A1 | 5/2008 | Besson |
| 2008/0210877 | A1 | 9/2008 | Altman et al. |
| 2008/0240341 | A1 | 10/2008 | Possin et al. |
| 2009/0154639 | A1 | 6/2009 | Nakanishi et al. |
| 2009/0173885 | A1 | 7/2009 | Zeitler et al. |
| 2009/0213985 | A1 | 8/2009 | Nakanishi et al. |
| 2009/0225955 | A1 | 9/2009 | Igarashi et al. |
| 2009/0252286 | A1 | 10/2009 | Mukumoto et al. |
| 2010/0002839 | A1 | 1/2010 | Yokota et al. |
| 2010/0067652 | A1 | 3/2010 | Shindo |
| 2010/0067767 | A1 | 3/2010 | Arakita et al. |
| 2010/0080338 | A1 | 4/2010 | Fukushima et al. |

(Continued)

*Primary Examiner* — Courtney Thomas
(74) *Attorney, Agent, or Firm* — McCarter & English, LLP (57) ABSTRACT

The present invention relates to systems and methods for reducing motion artifacts in x-ray sampling circuits. The detector system output is sampled at a rate than the x-ray exposure rate to reduce blurring associated with motion of the detector and/or object being scanned.

28 Claims, 11 Drawing Sheets

(56) References Cited

U.S. PATENT DOCUMENTS

| | | |
|---|---|---|
| 2010/0080433 A1 | 4/2010 | Noshi |
| 2010/0111393 A1 | 5/2010 | Okumura et al. |
| 2010/0135555 A1 | 6/2010 | Kobayashi et al. |
| 2010/0150421 A1 | 6/2010 | Nakanishi et al. |

* cited by examiner

DIGITAL INTEGRATION WITH DETECTOR CORRECTION

CROSS REFERENCE TO RELATED APPLICATION

This is a divisional application of U.S. application Ser. No. 12/628,774 filed Dec. 1, 2009, now U.S. Pat. No. 8,270,564 and claims priority to U.S. Provisional Application 61/118,793 filed on Dec. 1, 2008 the entire contents of the above patents and application being incorporated herein by reference.

BACKGROUND OF THE INVENTION

A CT or Computed Tomography scanning system can be used for many applications including imaging of the human anatomy in a medical imaging system as well as for baggage/container images in a security/inspection system. To form one frame of a CT image of a patent, for example, a scanner acquires roughly 1000 sequential X-ray exposures, each with 0.5 ms to 1 ms of exposure time. The X-ray transmission flux is measured at each of those 1000 exposures. The processed transmission flux measurements are then used to reconstruct an image which reveals the anatomical structures in a slice taken through the patient from the patient. There are artifacts associated with the detectors delays response from the current exposure and the decay responses of previous exposures, which leads to blurring of the acquired image. For helical scanning in which the object being scanned is moved there are additional artifacts associated with motion of the object which leads to blurring in an axial direction. Thus, a continuing need exists for improvements in CT scanning systems.

SUMMARY OF THE INVENTION

The present invention relates to x-ray imaging systems in which the detector system output is sampled at a rate to reduce motion artifacts. Digital integration with detector rise-and-fall time correction is used to reduce or eliminate image blurring associated with multiple sequential X-ray exposures.

An x-ray source emits x-ray radiation in a sequence of pulses at a selected exposure rate and detector output. A sampling circuit is used to sample the detector output at a rate higher than the x-ray exposure rate. In a preferred embodiment, analog-to-digital (A/D) converters can be used in sampling of the detector output signals. The A/D output clock rate is greater than the image exposure rate which enables correction based upon the detector's detection rise and fall characteristics. The detector elements in a given row can be multiplexed in the detector circuit.

DETAILED DESCRIPTION OF THE INVENTION

Figure 1:
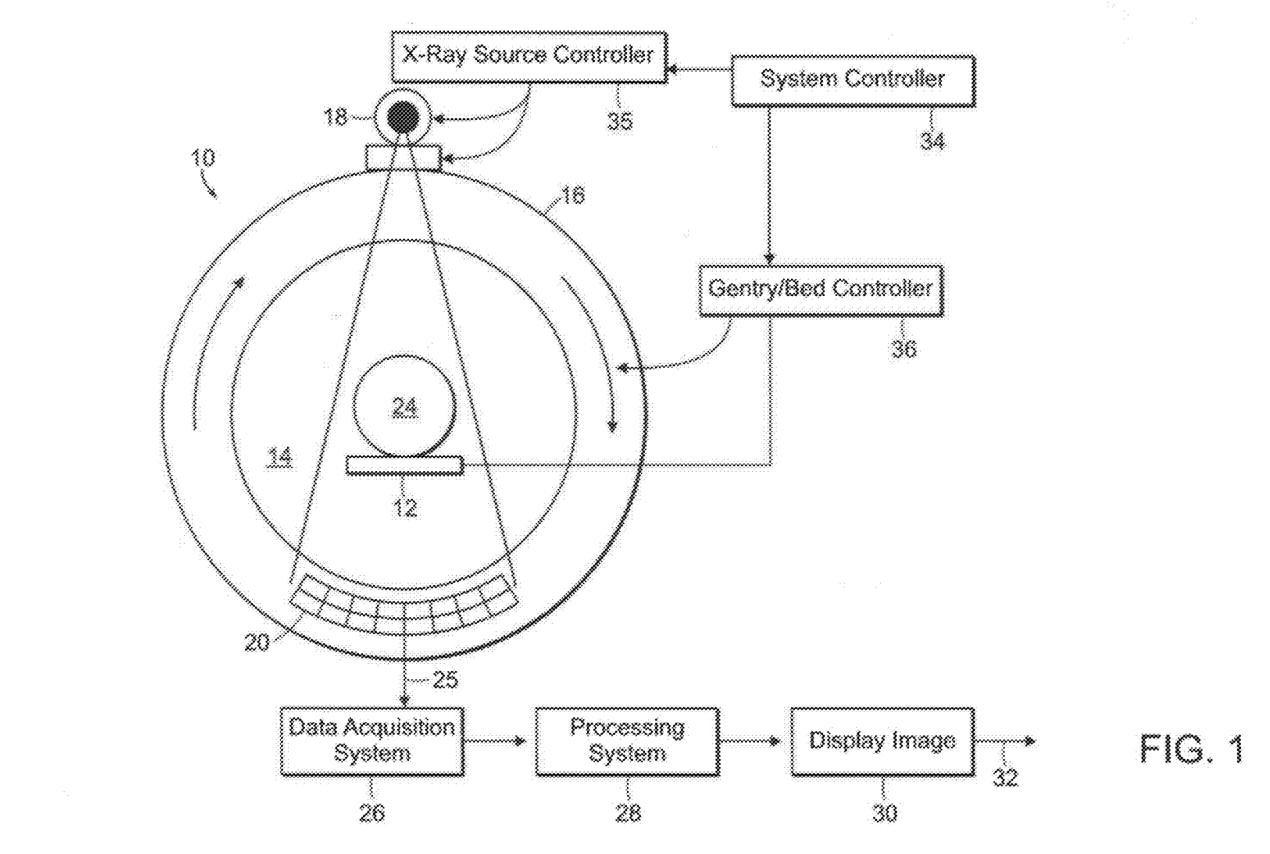
FIG. 1 is a schematic view of a CT scanner system is accordance with the invention.

As can be seen in FIG. 1, a CT scanner 10 includes of an object table or support 12 which is positioned within the center opening aperture 14 of a frame 16 or gantry. An x-ray source 18 is mounted within the gantry 16 to one side of the opening aperture 14, and a detector array 10 is mounted to the second side of the aperture 14. During scanning, the x-ray source and the detector array are rotated around the object 24. CT relies on the measurement of attenuated x-ray transmission flux through the object from different rotation angles to form an image. The X-ray flux after attenuation by an object impinging on the x-ray detector and the attenuated x-ray flux is measured and recorded using a data acquisition system 26, data processing system 28 and display 30. The images can then be transmitted 32 via wired or wireless connection to data storage or a network. A system controller 34 is connected to the x-ray source controller 35 and the gantry and support controller 36. the data acquisition system includes a sampling circuit device that samples the detector output signal 25 at a rte higher than the x-ray exposure rate. A preferred embodiment uses an analog-to-digital (A/D) converter that digitizes the detector output signals at a high resolution and speed.

Each attenuated measurement represents the summation or line integral of the attenuation coefficients of an object along a particular rotation angle or a ray path. Each set of measurements is referred to as a "view" or a "projection", and the measurement data of the complete set is referred to as a transmission profile. Typically, a 360 degree gantry rotation is used to acquire a complete transmission profile. During the 360 degree rotation, a typical CT scanner acquires roughly 1000 views, corresponding to 1000 different angular orientations, i.e., a single frame or a single slice of CT image comprises of roughly 1000 attenuated x-ray measurements. Each measurement corresponds to a particular angular orientation of the x-ray source and the detector array with an x-ray exposure time in a range of 0.1 to 5 millisecond and preferably of 0.5 to 1 millisecond (ms).

Figure 2A:
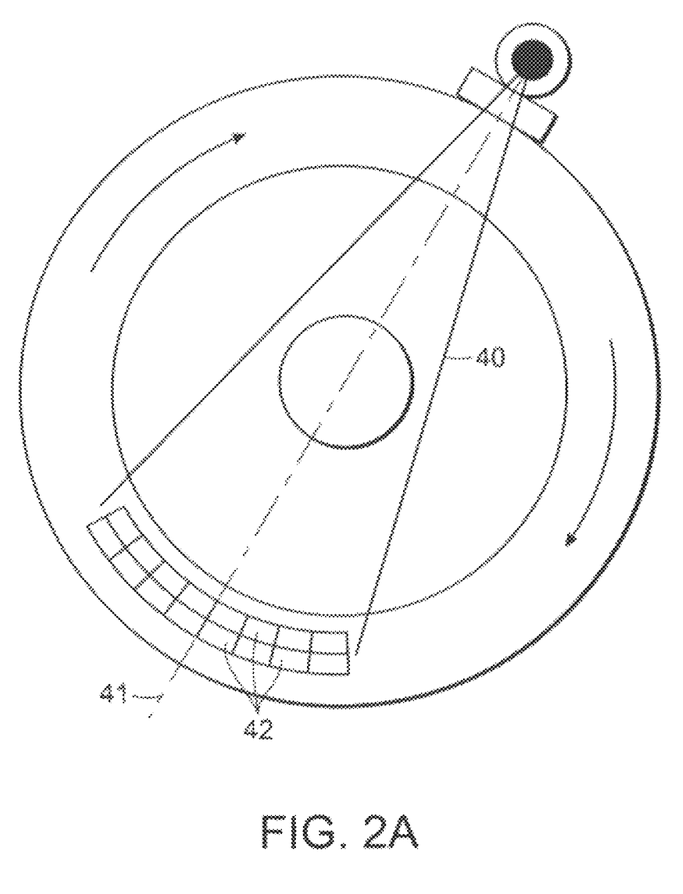
FIGS. 2A and 2B show different angular projections of an object being scanned.
Figure 2B:
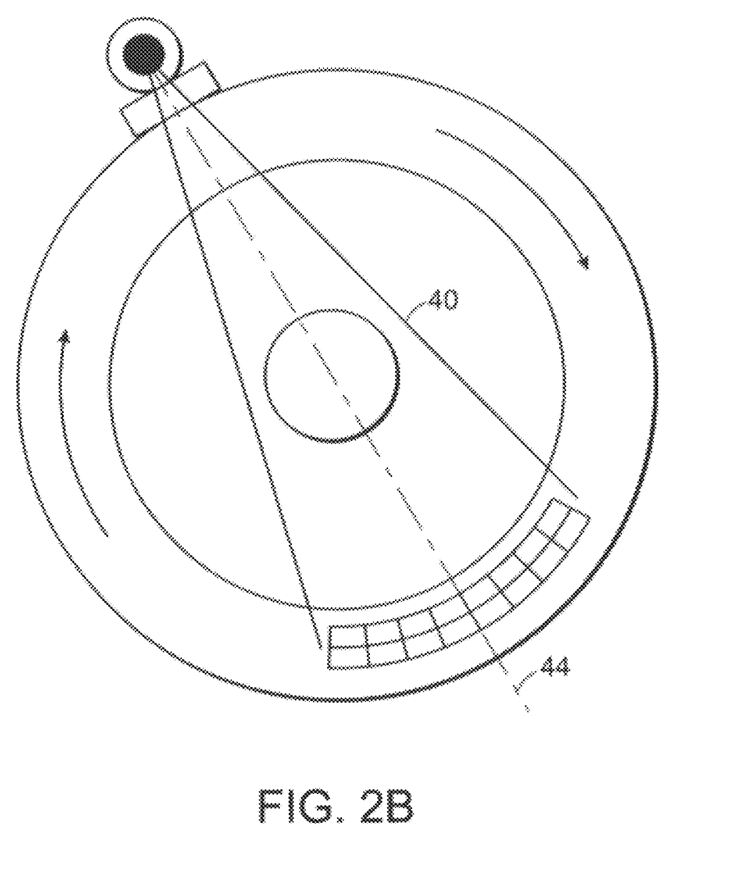
Figure 3:
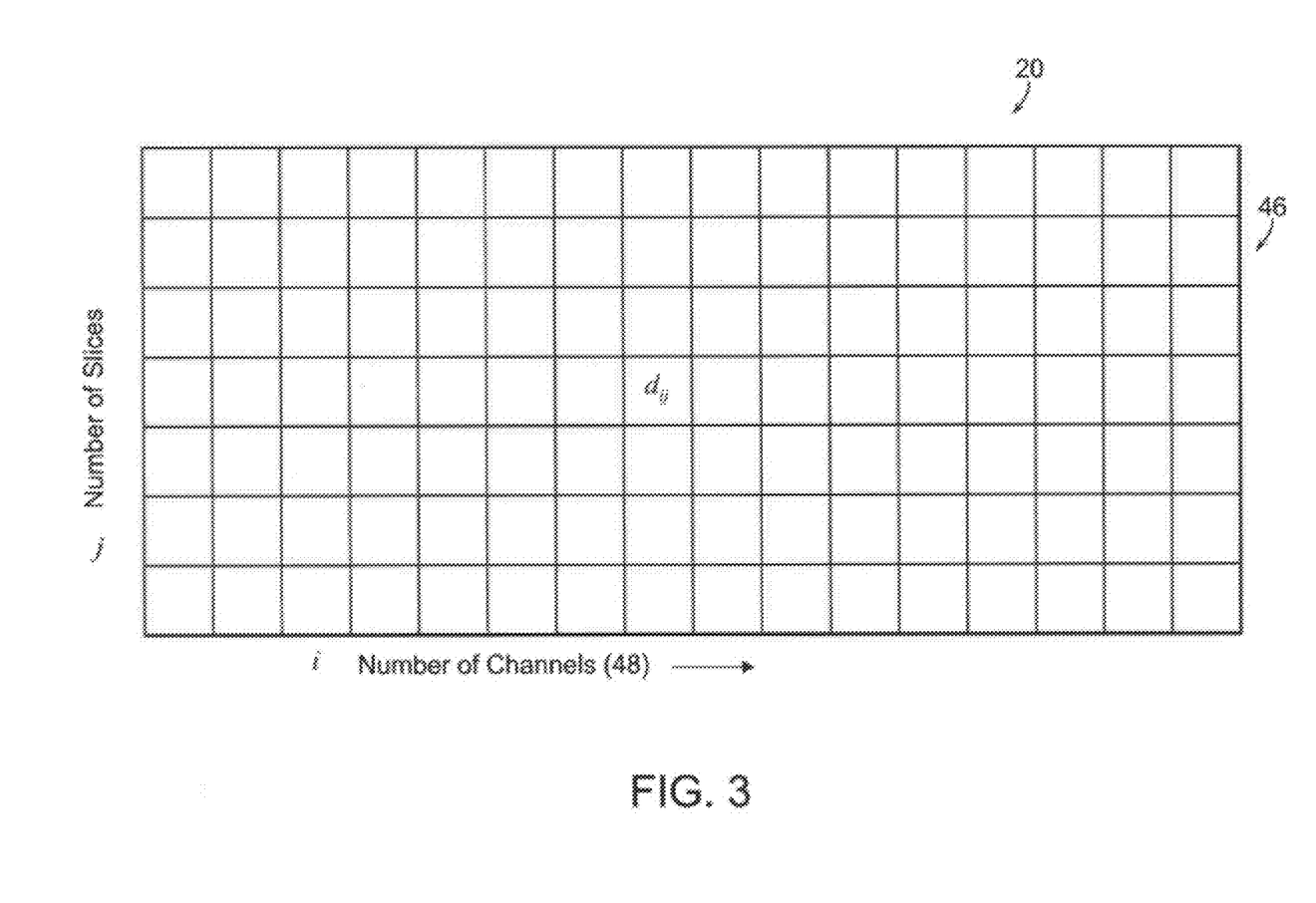
FIG. 3 shows a schematic view of a detector array having I rows and J columns of elements.

As shown in FIGS. 2A and 2B, the X-ray source produces a fan-shaped beam 40 that passes through the object and received by an array of detector elements 42. Each detector element 42 in this array produces a separate attenuation signal and the signals from all the detector elements produces the transmission profile for the indicated angular orientation. FIG. 2A reflects a fan beam directed along one axis 41 and FIG. 2B shows the fan beam directed along a second axis 44. The transmission profiles from all different angular orientations are then used to reconstruct an image which reveals the anatomical structures in a slice taken through the object. A typical scanner has 800 to 1000 detector elements or channels 48 along a row to provide fine resolution. A CT image generated by a single row of the detector array is referred to as a "slice". Conventionally, a CT scanner with a single row of detector array is referred to as a single slice CT, while a CT scanner that includes multiple rows 46 of such detector arrays is referred to as multi-slice CT, MSCT, or spiral CT. The number of slices corresponds to the number of rows of detector arrays. The MSCT was introduced in the early 1990s offering the benefit of simultaneous acquisition of multiple slices of images of the patient, allowing the acquisition of volume data without the danger of misregistraton or double registration of anatomical details. Recent generations of MSCT systems acquire more than 64 slices per rotation. As can be seen in FIG. 3, a detector array includes of i rows and j columns. A single pixel in the detector array is represented by $d_{ij}$ where i represents the detector channel number in a given row and j stands for slice number. In a medical CT scanner, typical element numbers of channels are 800 to 1000, typical slice numbers are 2, 4, 8, 16, 64, 256, etc.

Figure 4A:
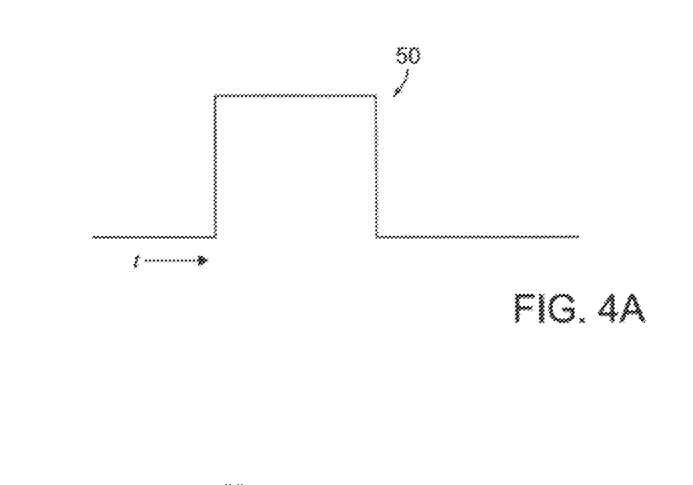
FIGS. 4A-4B are schematic graphical representations of a step function input waveform and a detected response, respectively.
Figure 4B:
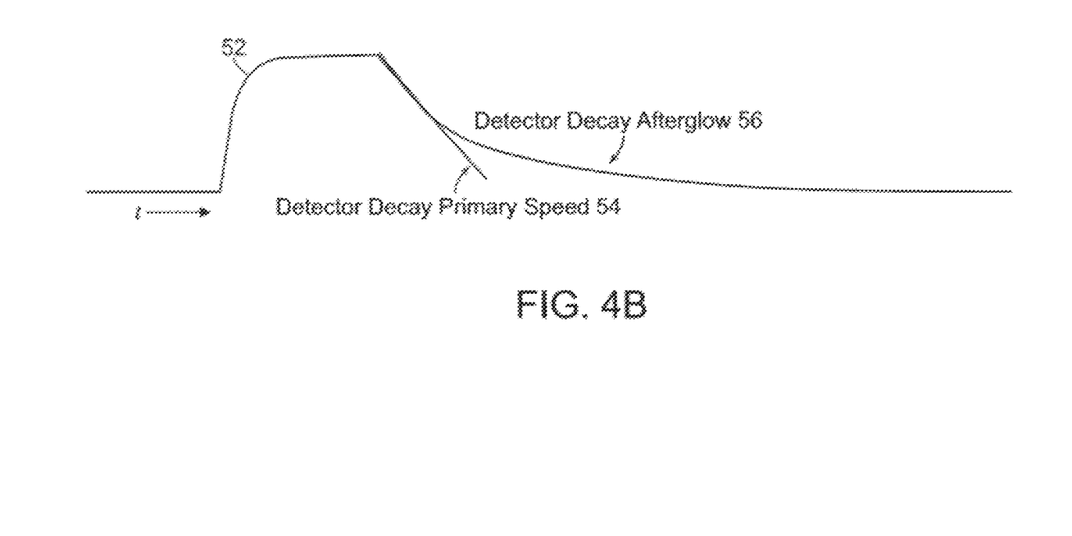

An x-ray detector can either be a photon counter or a solid state detector. The solid state detector offers the advantages of large packing density and are now most commonly used in all commercial CT scanners. Each solid state x-ray detector generally includes a scintillator and a solid state photodiode, or a solid state two dimensional array such as a CCD, (Charge Coupled Device). Direct x-ray detectors can also be used for certain applications. The scintillator converts the incoming x-ray photons into optical photons. When x-ray impinges on a scintillator, the optical photons are not emitted by the scinitallator instantaneously; rather the emission follows a long decay curve. Furthermore, when the impinging x-ray is shut off, the emission of photons are not terminated instantaneously; instead it has a long decay time. The slow rise-and-fall time of a detector is shown in FIG. 4B that is in response to an x-ray with a step function input waveform 50 shown in FIG. 4A. The detected response shown in FIG. 4B is characterized by a slow rise time 52 and a long decay time. The time dependence of the absorbed x-ray and the emitted photon intensity can be modeled as exponentials with different decay constants. In CT terminology, the decay time includes a primary decay factor 54 and after glow factor 56. The primary decay factor is the initial decay time constant. The remaining time constants are referred to as "after glow".

While measured x-ray transmission values can in principle be corrected arithmetically with slow (exponential) decay behavior, existing systems do not correct for the primary decay factor and initial after glow less than 0.5 ms. This results in poorer dynamic performance and higher computer costs associated with image processing. A preferred embodiment of the invention utilizes digital sampling system that corrects for effects due to both the primary speed and total after glow. Additionally, in helical scanning mode, where the object being scanned moves in an axial direction that is orthogonal to the plane of rotation of the source and detector while x-rays are being detected, can also create motion artifacts that can be addressed by the present invention. A preferred embodiment corrects each sub-sampled detector output before it is summed to provide the transmission profile. Thus, the present system corrects for overall cross channel blurring during helical scanning.

Typically in existing CT systems the read-out of each detector element occurs at the end of each total x-ray exposure at each selected angle of rotation. Thus the sampling time is about the same as the exposure time, i.e., about 0.5 ms to 1.0 ms. At the end of each exposure, the total integrated electrons are sampled and read-out. In the present invention, each detector can be exposed to the same x-ray transmission pulse sequence and the same total exposure time as existing systems, however, the read art is preferably at a much higher sampling rate. The output is converted to a digital representation and corrected for artifacts that occur during lead detection interval. The measured transmission profile at each view (angle) represents more exactly the alternated x-ray transmission. 2D and/or 3D image reconstruction can be carried out on the measured data to improve image quality and also reduce the x-ray exposure rate to increase patient safety.

Figure 5A:
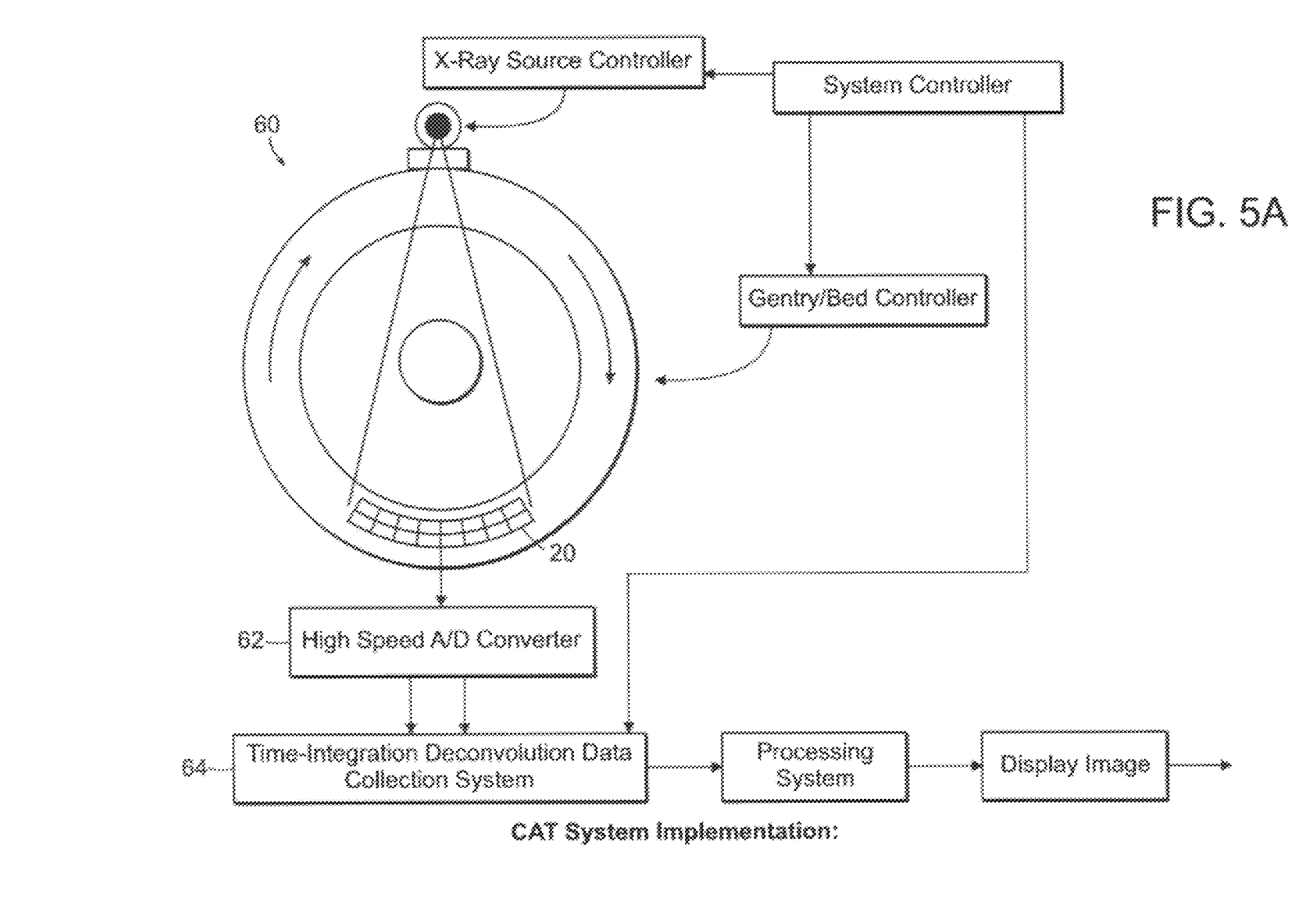
FIGS. 5A and 5B illustrate a preferred embodiment of a data acquisition system in accordance with the invention.
Figure 5B:
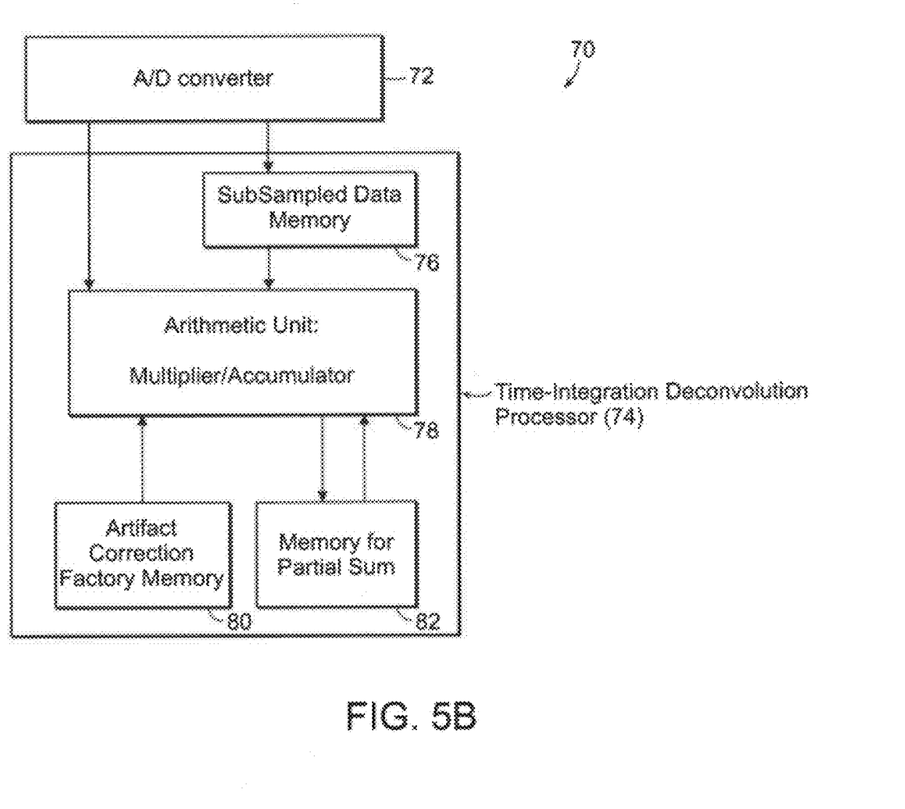

FIG. 5A illustrates a preferred embodiment of the invention in which the imaging system 60 as previously described has an A/D converter 62 receiving output signals from the detector 20. typically a 16-22 bit A/D is used where the converter operates at 1 kHz or more, preferably at 2 kHz or more. The output of the converter 62 is transmitted to a time integration deconvolution data collection system 64. An example 70 of such a system is shown in FIG. 5B. The output of converter 72 is transmitted to a sampled data memory 76 and an arithmetic unit 78 of processor 74. This also includes an artifact correction factor memory 80 and a memory 82 for partial summation.

In this example for a 64 slice by 1000 element detector array with a 0.5 second rotation rate collecting 1000 views each having 128 samples for each rotation, the A/D conversion rate is 128×64×2 k=16 MHz. If a more moderate 14 bit A/D converter is used, the bit accuracy is 21 bits. The partial sum indicated in Eq. (6) is stored in memory 82. Memory 80 is used to store the detector artifact correction factors from Eq. 6. The sum generated by arithmetic unit 78 is the alternated transmission corrected for primary speed and after glow.

The detector rise time response or the time dependence of the detector absorbed X-ray intensity can be modeled as $$R(t) = a_n(1 - e^{-t/\gamma_n}) \text{ for } t_{n-1} \leq t < t_n \quad (1)$$

where $a_n$ represents the relative strength of the scintillator's x-ray-photon-to-optical-photon response component with time constant $\tau_n$ and n is determined from measurements of the detector rise curve for a given incoming x-ray flux. For example, a scintillator's X-ray response with three time constants can be modeled with such as $$R(t) = a_1(1 - e^{-t/\gamma_1}) \text{ for } 0 \leq t < t_1$$

$$a_2(1 - e^{-t/\gamma_2}) \text{ for } t_1 \leq t < t_2$$

$$a_3(1 - e^{-t/\gamma_3}) \text{ for } t_2 \leq t < t_3 \quad (2)$$

The slope of a detector response at a given time t, R(t), is a unique function $$\frac{d}{dt}R(t) = \frac{a_n}{\tau_n}e^{-t/\gamma_n}$$

In particular, the initial slope $\dot{R}(0)$ can be expressed as $$\dot{R}(0) = \frac{a_1}{\tau_1} \quad (3)$$

The time dependence of the detector emitted light intensity can be modeled as follows, $$F(t) = b_m e^{-t/\tau_m} \text{ for } t_{m-1} \leq t < t_m \quad (4)$$

where $a_m$ represents the relative strength of the detector decay component with time constant $\tau_m$ and M is determined from measurements of the detector decay curve.

For example, it was reported in Kacheriess et al, "Advanced Single-Slice rebinning in conebeam Spiral CT," Med. Phys. 27, 754-772 (2000), the entire contents of which is incorporated herein by reference, $$F(t) = b_1 e^{-t/\tau_1} \text{ for } 0 \le t < t_1$$

$$b_2 e^{-t/\tau_2} \text{ for } t_1 \le t < t_2$$

$$b_3 e^{-t/\tau_3} \text{ for } t_2 \le t < t_3$$

$$b_4 e^{-t/\tau_4}, \text{ for } t_3 \le t < t_4 \qquad (5)$$

where $\tau_1 \sim 1$ ms, $\tau_2 \sim 6$ ms, $\tau_3 \sim 40$ ms and $\tau_4 \sim 100$ ms. Newer scintillation crystals having microsecond decay time with afterglow less than 0.1% of signal after 3 ms have been reported.

Figure 6A:
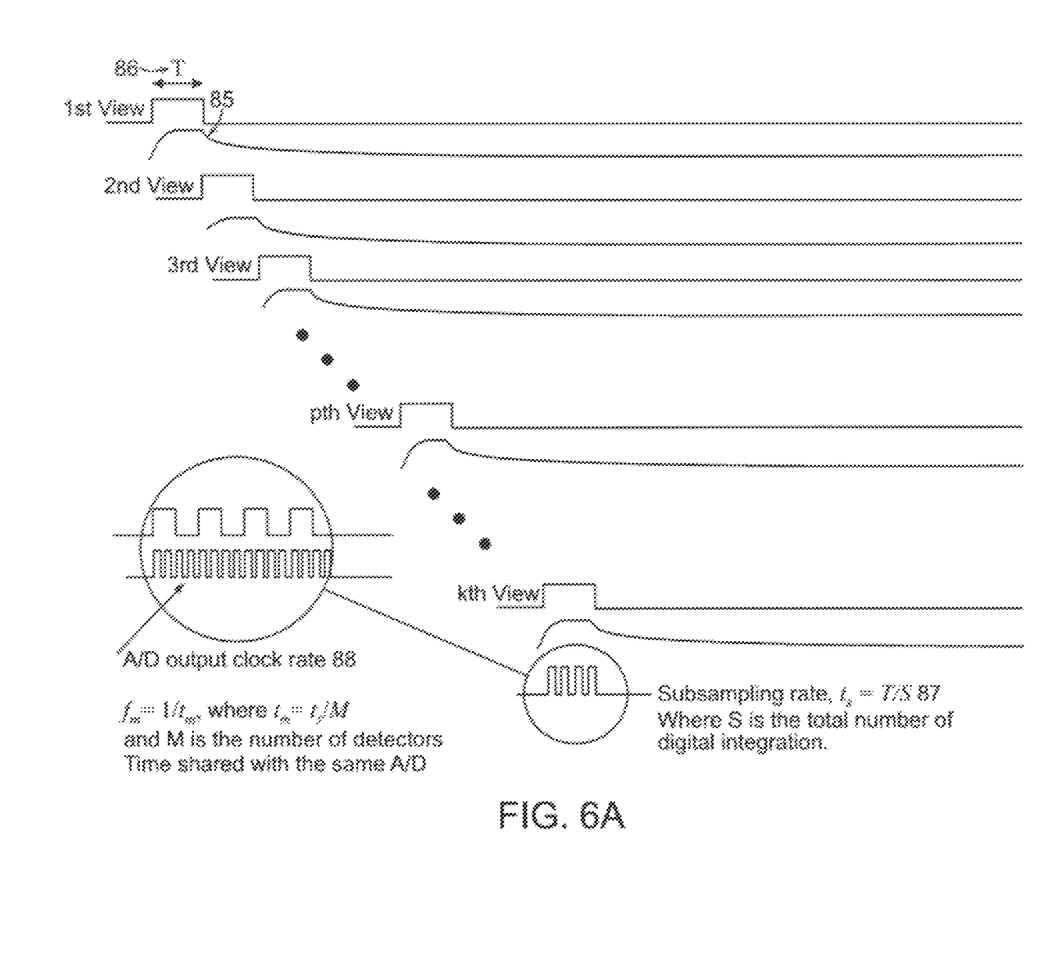
FIG. 6A illustrates measured detector response of the first to the $k^{th}$ view and the sub-sampling rate.

As the detector array rapidly rotates about the patient, the exponential decay blurs together detector readings for successive views. As shown in FIG. 6A, the measured detector response at $k^{th}$ view, includes the detector response 85 due to the $k^{th}$ X-ray exposure also all (k-1) previous x-ray exposures each at interval 86. Those exponential decay blurring terms, due to the response time lag of the detector, is referred to as the "primary speed" term and the "after glow" term, whereas the "primary speed" refers to the primary decay component of the detector and the "after glow" refers to all the remaining components. The primary speed of the detector degrades the spatial resolution of the system, and the afterglow term degrades the azimuthal component of the image resolution. As shown above, the primary speed of a typical commercially used X-ray detector is about 1 ms. As stated above, a typical CT system acquires roughly 1000 views over a 360° rotation, the sampling time of each view is chosen to be about the same as the primary speed decay time constant of the detector. In currently available CT systems, corrective algorithms have been reported to compensate for the detector after glow decay characteristic but not to correct for the primary speed term. The present invention provides an X-ray sampling system and method that allows correction for both "primary speed" term, the "after glow" term of the emitted-light decay time constant and also provides for correction for the detector slow rise time of the absorbed X-ray.

Instead of using the detector to integrate the total X-ray exposures during each view, the present invention measures the detector outputs using a much higher sub-sampling rate 87 within each exposure, digitizing the higher sub-sampling rate samples, correcting the samples based on the detector rise-and-fall characteristics stored in memory 80 and then digitally integrating the corrected samples for the total exposure time of each view. For example, for a CT scanner with a 0.5 s rotation and a 1000 views, the system utilizes a 0.5 ms exposure time or a 2 Khz sampling rate at each view. In this invention, an A/D converter is used to sample the detector outputs at a sub-sampling rate 88 of 64 kHz, preferably 128 kHz or more, or at a 7.8 μs intervals, i.e., a total of 64 samples are collected during each view. Each collected digital sample will be compensated for its detector decay time constants based on Equations (1) to (5).

It can be seen from FIG. 6A the detector output at the $k^{th}$ view is the sum of all the sub-samplings during this period with the detector outputs properly compensated for both the detector rise time of the $k^{th}$ view, also for the decay responses from all the previous k-1 views. Let T represents CT's sampling time for each view, or the exposure time at each view, and let S be the total sub-sampling number of this invention. Define $t_s = T/S$, where $t_s$ is the sub-sampling time of the CT system and s is the running index representing the sub-sampling time. As described above and shown in the process of FIG. 6B, for example, for a given CT scan parameter are selected 91, the X-ray exposure time or the sampling time of each view is 0.5 ms, let us take 64 subsamples during this exposure time, it follows than $t_s = 0.5$ ms/64 = 7.8 us, or the sub-sampling rate is 128 KHz. The operation principle is as follows.

1. At any sub-sampling time of the first viewing angle, k=1, the transmit-attenuated detector input signal impinging at detector located at the $i^{th}$ column and $r^{th}$ row, $x_{ij}(st_s)$ is the measured detector output, $y_{ij}(st_s)$, compensated by its rise time.

$$x_{ij}(st_s) = y_{ij}(st_s)/a(1 - e^{-st_s/\gamma 11})$$

where $\gamma_1$ is the detector initial rise time constant.

2. At any sub-sampling time of the second $2^{nd}$ viewing angle, k=2, the detector input signal, $x_{ij}(T+st_s)$ is the sum of the measured output $y_{ij}(T+st_s)$ compensated by the detector's rise-time response and the decayed output due to the input X-ray impinging at the detector at first viewing angle, $x_{ij}(1)$ $$x_{ij}(T+st_s) = y_{ij}(T+st_s)/a(1 - e^{-st_s/\gamma 11}) - x_{ij}(st_s) b_1 e^{-st_s/\tau_1}$$

where $\tau_1$ is the detector primer decay constant.

3. At any sub-sampling time of the $3^{rd}$ view, the detector input signal, $x_{ij}(2T+st_s)$ is the sum of the measured output, $y_{ij}(2T+st_s)$ compensated by the detector's rise time response, the decayed output due to the input X-ray impinging at the detector at first viewing angle, $x_{ij}(T)$ and the decayed output due to the input X-ray impinging at the detector at second viewing angle, $x_{ij}(2T)$.

$$x_{ij}(2T+st_s) = y_{ij}(2T+st_s)/a(1 - e^{-st_s/\gamma 11}) - x_{ij}(T+st_s) b_1 e^{-st_s/\tau_1} - x_{ij}(st_s) b_2 e^{-(T+st_s)/\tau_2}$$

where $\tau_2$ is the decay time constant for $T \le t < 2T$.

4. At any sub-sampling time of the $k^{th}$ view, the detector input signal, $x_{ij}(kT+st_s)$ is the sum of the measured output, $y_{ij}(kT+st_s)$ compensated by the detector's rise time response, the decayed outputs due to the input X-ray impinging at the detector at all previous viewing angles, 1, 2, . . . k-1, ie., $x_{ij}(1)$, $x_{ij}(2)$, . . . , $x_{ij}(k-1)$.

It can be seen that the input signal impinging on the detector, or, $x_{ij}(kT, st_s)$ can be expressed as $$x_{ij}(kT+st_s) = y_{ij}(kT+st_s)/a(1 - e^{-st_s/\gamma 11}) - x_{ij}((k-1)T+st_s) b_1 e^{-st_s/\tau_1} - x_{ij}((k-2)T+st_s) b_2 e^{-(st_s+T)/\tau_2} - \ldots - x_{ij}(T+st_s) b_k e^{-(st_s+(k-1)T)/\tau_k} \qquad (6)$$

Figure 6B:
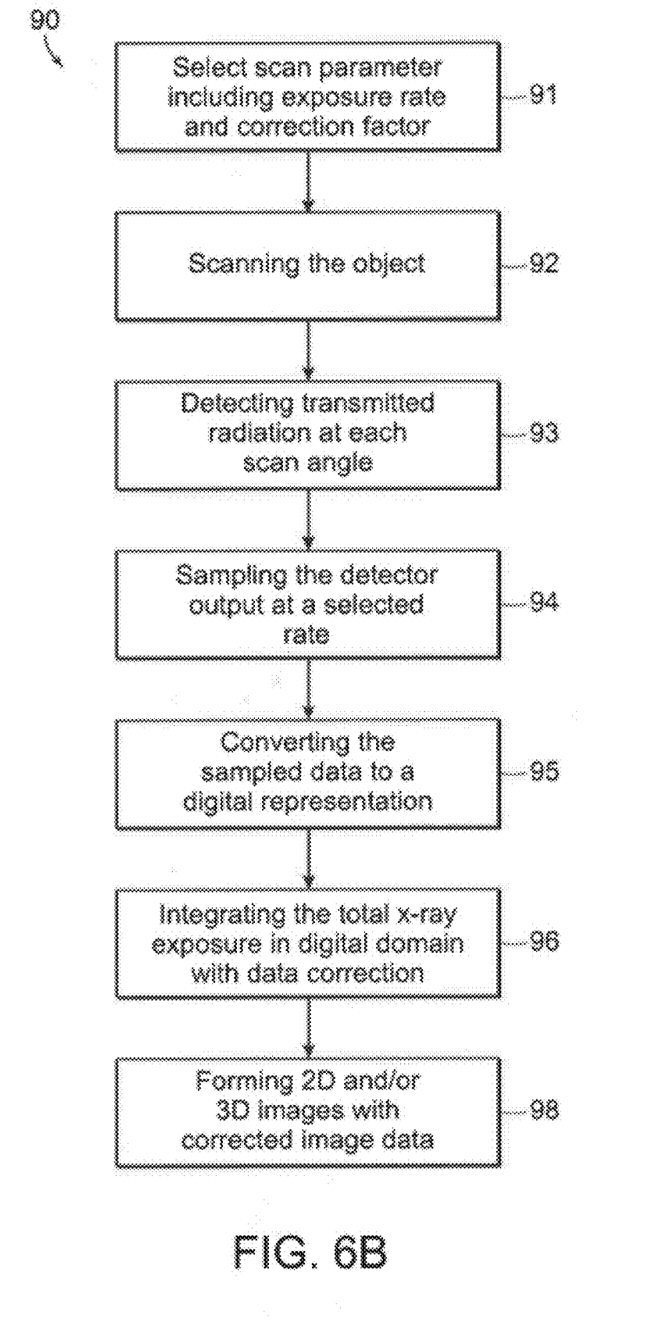
FIG. 6B illustrates a process sequence for acquiring a two or three dimensional image of an object such as an animal or human body in accordance with the invention.

Following scanning 92, detection 93, sampling 94, and conversion 95, the corrected sample 96 is then summed with the next acquired, corrected sample until the total viewing time is completed for imaging 98, i.e., the detector input signal at the end of the $k^{th}$ view can be expressed as $$x_{ij}(kT) = \sum_{s=1}^{S} x_{ij}((k-1)T + st_s) \qquad (7)$$

As can be seen from the about detector decay constant samples, a typical detector has time varying decay constants at the initial exposure of the X-ray flux, after several tenth ms, the detector reaches a final state of decay constant. At the $k^{th}$ view, only the last $(k-p)^{th}$ views with time constants that is time varying, all the previous $(k-p-1)^{th}$, . . . , k3, k2, k1 views already reached to the final steady state "after glow" decay time constant. Let us define $$P_{ij}(pT)=x_{ij}(p-1)e^{-T/\tau_p}+x_{ij}(p-2)e^{-2T/\tau_p}-\ldots -x_{ij}(1)e^{-(p-1)T/\tau^p}$$

It follows then $$x_{ij}(kT+st_s)=y_{ij}(kT+st_s)/(1-e^{-st_s/\tau_1})-x_{ij}((k-1)T+st_s)b_1 e^{9-sts/\tau_1}-x_{ij}((k-2)T+st_s)b_2e^{-(T+sts)/\tau_2}-\ldots -e^{-t_s/\tau_p}P_{ij}(pT)$$

As stated before, the detector input signal at the end of the $k^{th}$ view can be expressed as $$x_{ij}(kT) = \sum_{s=1}^{S} x_{ij}((k-1)T+st_s)$$

In summary, the attenuated X-ray transmission flux through the object from given rotation angle k at the end of $k^{th}$ view, $x_{ij}(k)$, is the sum of all the sub-samplings during this period with the detector outputs properly compensated for both the detector rise time of the $k^{th}$ view, also for the decay responses from all the previous k−1 views.

In the above, only a single detector response has been described. It follows that in a multi-slice CT system, there are $x_{ij}(k)$ detector responses, where j=1, 2, . . . , J, represents number of slices of the CT scanner, and i=1, 2, . . . , 1, represents number of detectors in a given row, and. Currently, there are single slice, double slices, 4 slices, up to 64 slices CT scanner in production, and there are 256 slices prototype systems.

A high-resolution, high-speed (i.e., >60 Mhz), bit-serial A/D is used in this implementation. The A/D outputs can be a series 12 bits as opposed to having 12 parallel digital output bits. In this way the number of I/O pins and I/O communication wires of the signal processing boards are significantly reduced. Each serial digital output bits may be in the form of low voltage differential signaling (LVDS). The ADC with LVDS outputs have no difficulty in driving cables directly, but the quality of the cable determines the maximum frequency the cable can carry. The signal from the LVDS can be transmitted over 2 meter cable.

Let us summarize the proposed implementation.
- i=1, 2, . . . . I, represents the number of channels within each row of the detector array. Typical channel numbers are 800, 1000, i.e., generally in a range of 500 to 2000 channels;
- j=1, 2, . . . . J, represents the number of rows within each director array, or represents number of slices of the CT scanner. Typical slice numbers are 1, 4, 8, . . . 64, 128, 256;
- k=1, 2, . . . , K, represents the number of views of a given CT image, typical views are about 1000;
- T=detector dwell time of a given view/orientation angle, typical view time is about 0.5 ms to 1 ms;
- s=1, 2, . . . S, represents the number of sub sampled transmission data, typical total sub sample are 64, 128, 256;
- $t_s$=T/S, detector sub-sampling time within each view, where S represents the total subsampling integration number, Typical S are 64, 128, 256, etc;
- $t_m=t_s/M$ represents detector output multiplex time, where M represents the number of detectors time sharing a single A/D converter. Typical M is 4, 8, . . . , 32, 64, etc;
- A Bit-serial output A/Ds are used to reduce the number of I/O cables, the available bit-serial A/Ds are list in Table 1;
- The digitized X-ray output data are corrected based on the detector rise-and-fall time characteristic and then all "S" sub-sampled data are digitally summed to generated the output of a given view.

Figure 7:
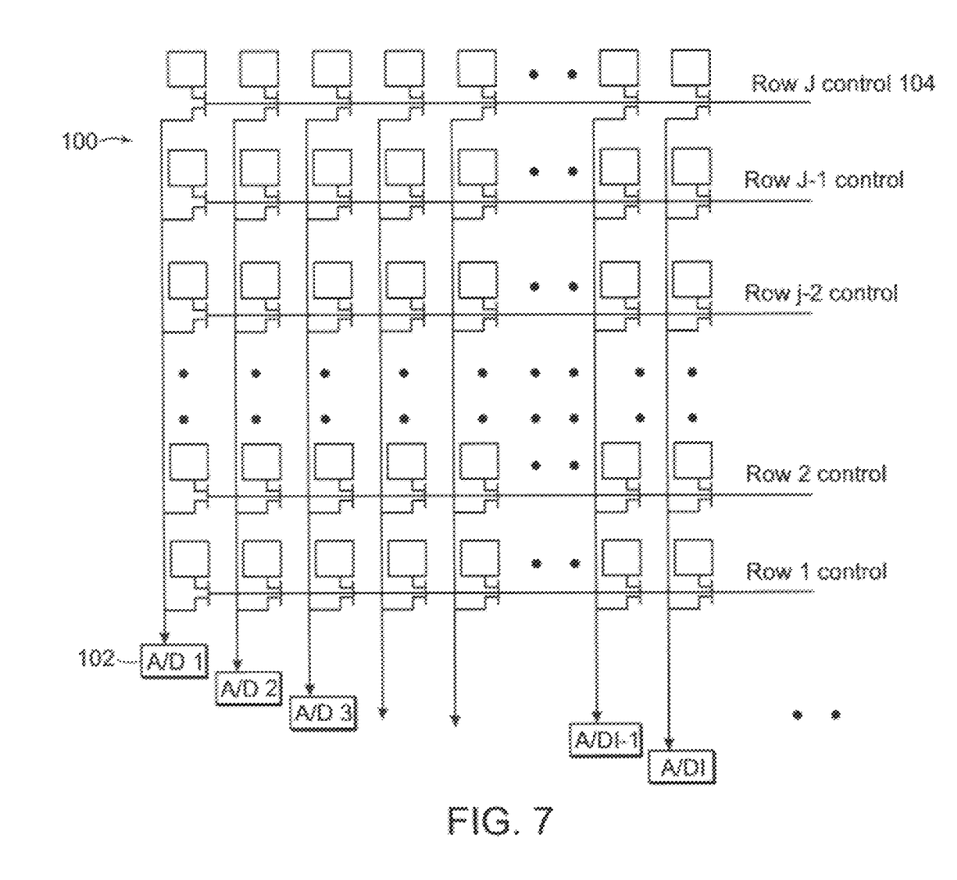
FIG. 7 illustrates a transistor array for a preferred embodiment of the invention.
Figure 8:
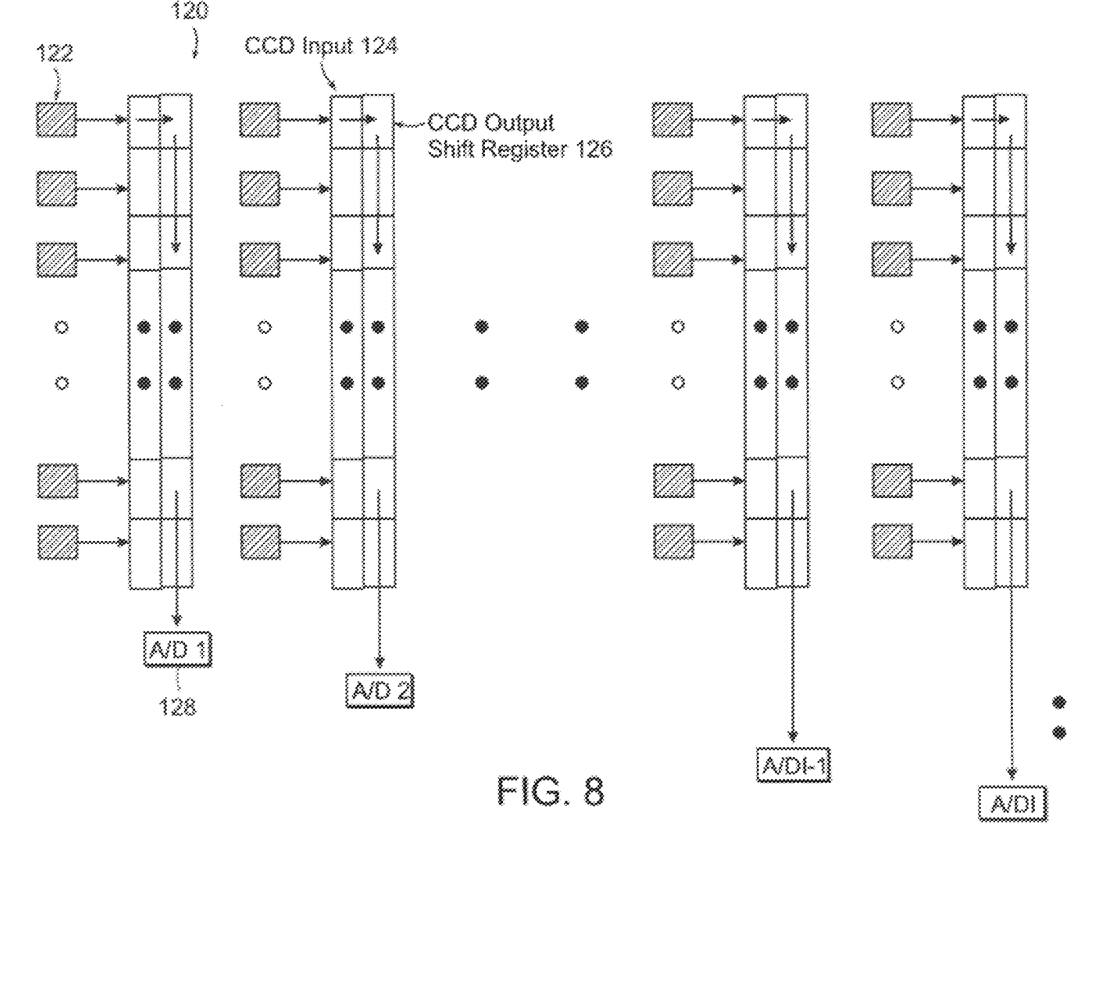
FIG. 8 illustrates an array of CCD output shift registers, each associated with the detector and data acquisition system.

The time multiplexed detector output can be implemented within the detector array 100, as can be seen in FIG. 7, the output of each photodiode element is connected to a switching transistor. All the switch transistors on a given row 104 have a common control, ie, for a detector array with J-row elements, there are J-control lines. Within each sub-sampling time, $t_s$, a single impulse is clocked propagating through the J-control lines, which in turn allows the outputs of the photodiodes of each column be sequentially readout at a clock rate of $f_m=1/t_m$, where $t_m=t_s/M$ and M is the total number of photodiodes timing sharing a single A/D 102. In a CCD detector array 120 implementation, as shown in FIG. 8, charge from the photodiode array 122 of each column are parallel transferred 124 to a CCD parallel-in-serial-out output shift register 126 at the end of sub-sampling time $t_s$, all the charges within the shift register are then serially clocked out at a clock rate of $f_m=1/t_m$.

For the example of a CT scanner with a detector dwell time T be 0.5 ms. Let the total number of subsampling be 64, it follows then $t_s$ be 7.8 us. Consider a 64-slice CT scanner, and let all the detectors along a given column share a single high-speed, bit-serial A/D. A single 60 MHz A/D is more than adequate to handle the entire detector along a given column. That is to say, for a 64 slice 1000 element CT scanner only 1000 A/D converters needs to be used, because all 64 elements in a given channel position can time-share the same A/D. For the above sample, the muxed detector output sampling rate, $t_m$, is only 8 Mhz. As seen in Table 1, either Analog Device AD9222-50 or TI AS 5272 can be used for this application. Furthermore both A/D converter's provide LVDS bit serial output. So, a 64-dice CT scanner with 1000 detector channels within each slice only needs 1000 pairs of LVDS digital outputs clocked at 96 MHz.

TABLE 1

|  | ADS5270 | ADS5271 | ADS5272 | ADS5273 | ADS5277 |
|---|---|---|---|---|---|
| Resolution (Bits) | 12 | 12 | 12 | 12 | 10 |
| Sample Rate (max) | 40 MSPS | 50 MSPS | 65 MSPS | 70 MSPS | 65 MSPS |
| Architecture | Pipeline | Pipeline | Pipeline | Pipeline | Pipeline |
| # Input Channels (Diff) | 8 | 8 | 8 | 8 | 8 |
| Power Consumption (Typ)(mW) | 907 | 957 | 983 | 1003 | 845 |
| SINAD (dB) | 70 | 70 | 71 | 70.8 | 61.7 |
| SNR (dB) | 70.5 | 70.5 | 71.1 | 71.1 | 61.7 |
| SFDR (dB) | 85 | 85 | 85 | 85 | 85 |

TABLE 1-continued

|  | ADS5270 | ADS5271 | ADS5272 | ADS5273 | ADS5277 |
|---|---|---|---|---|---|
| No Missing Codes (Bits) | 12 | 12 | 12 | 12 | 9.7 |
| ENOB (Bits) | 11.3 | 11.3 | 11.5 | 11.5 | 10 |
| Analog Voltage AV/DD (Min)(V) | 3 | 3 | 3 | 3 | 3 |
| Analog Voltage AV/DD (Max)(V) | 3.6 | 3.6 | 3.6 | 3.6 | 3.6 |
| Input Type | Voltage | Voltage | Voltage | Voltage | Voltage |
| Analog Input 8 W (MHz) | 300 | 300 | 300 | 300 | 300 |
| No. of Supplies | 1 | 1 | 1 | 1 | 1 |
| Pin/Package | 80HTQFP | 80HTQFP | 80HTQFP | 80HTQFP | 80HTQFP |
| Approx. 1 KU Price (US$) | 44.00 | 48.00 | 54.65 | 121.00 | 32.00 |
|  | Samples Inventory | Samples Inventory | Samples Inventory | Samples Inventory | Samples Inventory |

The claims should not be read as limited to the recited order or elements unless states to the effect. All embodiments that come within the scope and spirit of the following claims and equivalent thereto are claimed as the invention.

What is claimed is:

1. A sampling circuit for a computed tomography imaging system comprising:
   a sampling circuit that samples an x-ray detector output at a higher rate than an x-ray exposure rate of the computed tomography imaging system;
   the sampling circuit including an analog to digital (A/D) converter that digitizes the x-ray detector output.

2. The sampling circuit of claim 1 wherein the sampling circuit corrects sub-sampled data according to a rise-and-fall characteristic of the x-ray detector, and that sums the sub-sampled data within each view to generate an image.

3. The sampling circuit of claim 1 wherein the A/D converter comprises a bit-serial A/D converter sampling circuit.

4. The sampling circuit of claim 1 wherein the A/D converter comprises an LVDS bit-serial A/D converter.

5. The sampling circuit of claim 1 comprises a plurality of A/D converters.

6. The sampling circuit of claim 1 wherein the A/D converter generates A/D converter outputs that are transmitted by wireless transfer to a signal processor.

7. The sampling circuit of claim 1 wherein the sampling circuit adjusts the sub-sampled data using a motion parameter of an object.

8. The sampling circuit of claim 1 wherein the sampling circuit further comprises a sampled data memory.

9. The sampling circuit of claim 1 wherein the sampling circuit further comprises a multiplexer.

10. The sampling circuit of claim 1 wherein the sampling circuit further comprises an artifact correction factor memory.

11. The sampling circuit of claim 1 wherein the sampling circuit further comprises a memory for partial summation.

12. The system of claim 1 further comprising a controller connected to an x-ray source of the imaging system and a sampled data processor.

13. The system of claim 1 wherein the imaging system further comprises a patient support configured such that relative movement between the patient and the gantry can be actuated.

14. The system of claim 1 wherein the imaging system further comprises a memory for storing a time curve characteristic of the detector.

15. The system of claim 1 wherein the detector comprises a multi-slice detector array.

16. The system of claim 1 further comprising detector output shift registers connected to a plurality of A/D converters.

17. A method of sampling a detector output for computed tomographic imaging of an object comprising:
   generating image data from detected radiation transmitted through an object with a detector during rotation of an x-ray source and a detector through at least 360 degrees at a selected rotation rate, the detector generating detected radiation signals;
   sampling the detected radiation signals with a sampling circuit operating at a sampling rate greater than an exposure rate of the x-ray source; and
   irradiating an object at different angles at the exposure rate with the x-ray source mounted on a gantry with the detector.

18. The method of claim 17 further comprising converting detected radiation from an analog to digital format with the sampling circuit.

19. The method of claim 17 further comprising scanning a patient with a multislice computed tomography device which rotates the detector through at least 360 degrees.

20. The method of claim 17 further comprising storing a response time characteristic of the detector in a memory.

21. The method of claim 20 further comprising storing the response time characteristic that includes a plurality of blurring terms including detector rise time, primary speed and after glow.

22. The method of claim 17 further comprising obtaining 64 or more image slices per 360 degree rotation.

23. The method of claim 17 further comprising adjusting the sampled data using a motion parameter of the object.

24. The method of claim 17 further comprising using a controller connected to the x-ray source and a sampled data processor.

25. The method of claim 24 wherein the sampled data processor further comprises a sampled data memory.

26. The method of claim 18 wherein the converting step comprises operating an A/D converter at 1 kHz or more.

27. The method of claim 17 further comprising scanning an object with a fan beam.

28. The method of claim 17 further comprising positioning a patient on a table and actuating relative movement between the patient and the gantry.

* * * * *